(12) United States Patent
Koller et al.

(10) Patent No.: US 6,753,161 B2
(45) Date of Patent: *Jun. 22, 2004

(54) OPTOINJECTION METHODS

(75) Inventors: Manfred R. Koller, San Diego, CA (US); Elie G. Hanania, San Diego, CA (US); Timothy M. Eisfeld, San Diego, CA (US); Bernhard O. Palsson, La Jolla, CA (US)

(73) Assignee: Oncosis LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/961,691

(22) Filed: Sep. 21, 2001

(65) Prior Publication Data

US 2002/0076744 A1 Jun. 20, 2002

Related U.S. Application Data

(63) Continuation-in-part of application No. 09/728,281, filed on Nov. 30, 2000, now Pat. No. 6,514,722, which is a continuation-in-part of application No. 09/451,659, filed on Nov. 30, 1999, now Pat. No. 6,534,308, which is a continuation-in-part of application No. 09/049,677, filed on Mar. 27, 1998, now Pat. No. 6,143,535, which is a continuation-in-part of application No. 08/824,968, filed on Mar. 27, 1997, now Pat. No. 5,874,266.

(51) Int. Cl.[7] .................... G01N 33/48; C12N 13/00; C12N 1/18; C12N 1/38; C12M 1/22

(52) U.S. Cl. ............. 435/40.5; 435/173.1; 435/244.1; 435/244.2; 435/244.3; 435/244.4; 435/254; 435/255; 435/256; 435/288.7

(58) Field of Search .............. 435/40.5, 173.1, 435/244, 254, 255, 256, 288.7, 240.1, 240.2, 240.3, 240.4

(56) References Cited

U.S. PATENT DOCUMENTS

5,013,660 A * 5/1991 Kasuya et al.
6,143,535 A * 11/2000 Palsson

OTHER PUBLICATIONS

Guo et al., "Laser–mediated Gene Transfer in Rice," *Physiol. Plantar.*, 93:19–24 (1995).

Krasieva et al., "Mechanisms of Cell Permeabilization by Laser Microirradiation," LAMMP, Beckman Laser Institute, University of California at Irvine, Irvine, California, 8 pp., SPIE Proceedings (1999).

Palumbo et al., "Targeted Gene Transfer in Eucaryotic Cells by Dye–assisted Laser Optoporation," *J. Photochem. Photobiol.*, 36:41–46 (1996).

Soughayer et al., "Characterization of Cellular Optoporation with Distance," *Anal. Chem.*, 72:1342–1347 (2000).

* cited by examiner

*Primary Examiner*—Jon P. Weber
*Assistant Examiner*—Kailash C. Srivastava
(74) *Attorney, Agent, or Firm*—McDermott Will & Emery

(57) ABSTRACT

Optoinjection method for transiently permeabilizing a target cell by (a) illuminating a population of cells contained in a frame; (b) detecting at least one property of light directed from the frame; (c) locating a target cell by the property of light; and (d) irradiating the target cell with a pulse of radiation.

60 Claims, 10 Drawing Sheets

Optoinjection of TR-Dextran

Fig. 8A: All Cells

Fig. 8B: TR-Dextran

Fig. 8C: Dead Cells

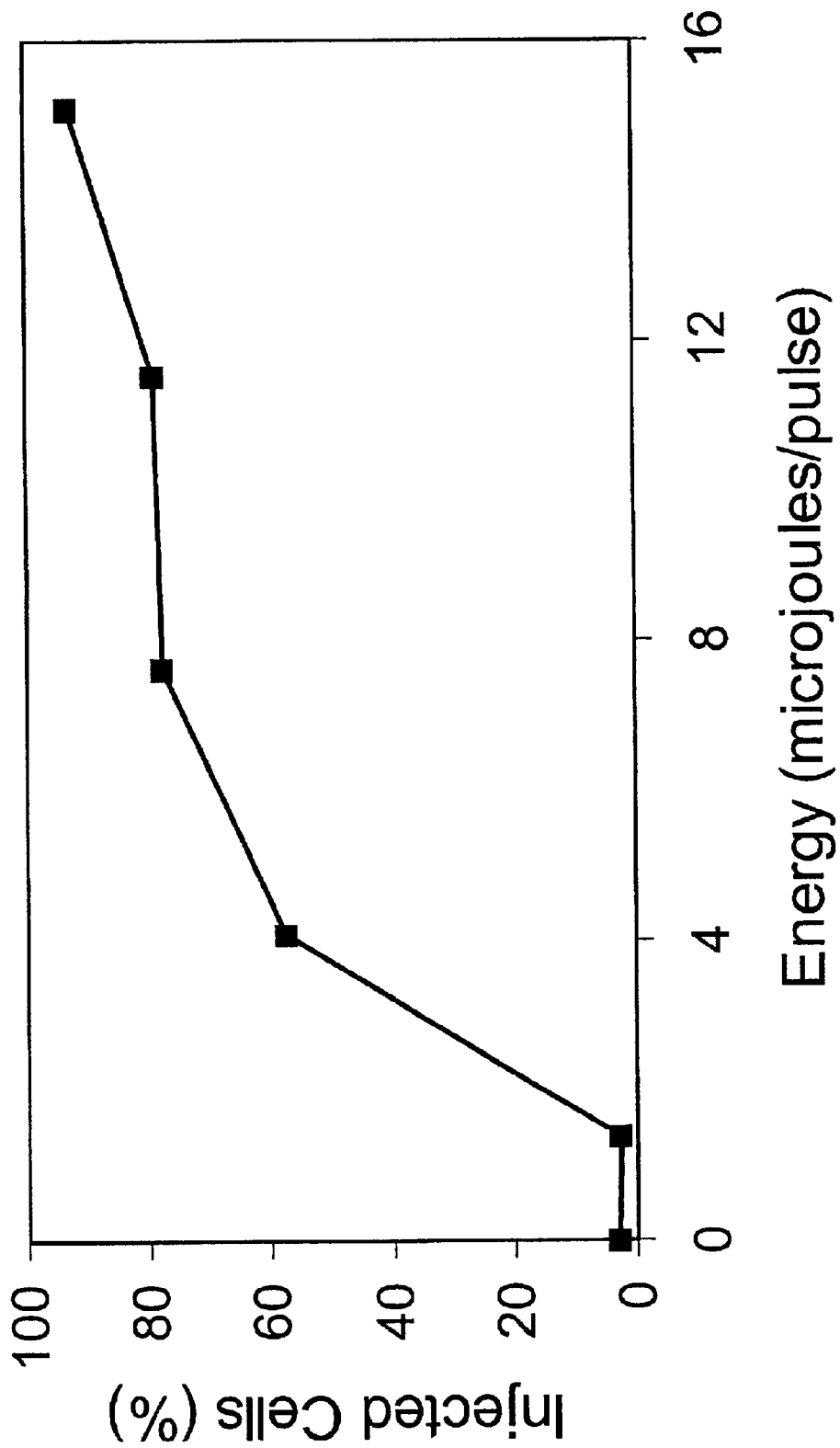

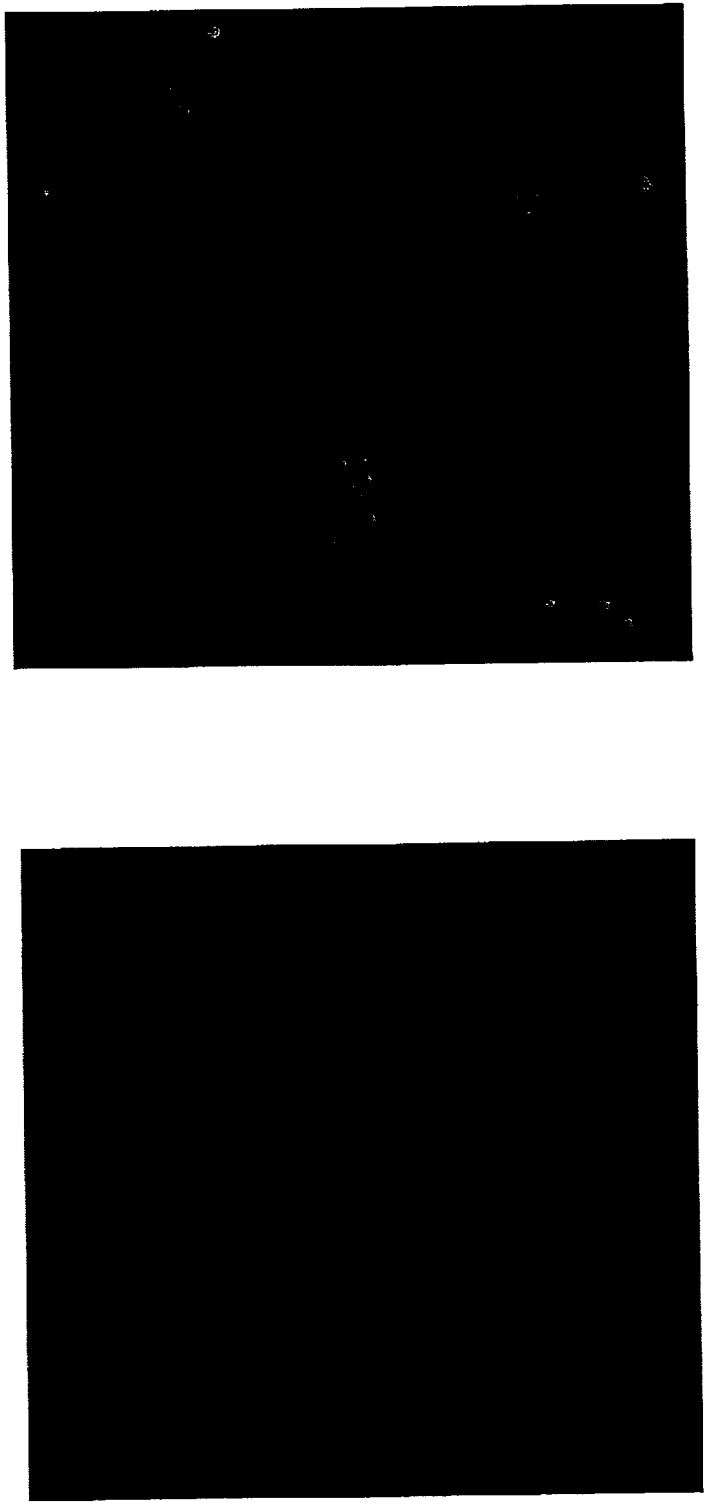
Figures 10A, 10B: Optoinjection of Plasmid
Fig. 10A: Control
Fig. 10B: Optoinjected

OPTOINJECTION METHODS

This application is a continuation in part of U.S. patent application Ser. No. 09/728,281, filed Nov. 30, 2000, now U.S. Pat. No. 6,514,722; which is a continuation in part of application Ser. No. 09/451,659, filed Nov. 30, 1999, now U.S. Pat. No. 6,534,308; which is a continuation in part of application Ser. No. 09/049,677, filed Mar. 27, 1998, now U.S. Pat. No. 6,143,535; which is a continuation in part of application Ser. No. 08/824,968, filed Mar. 27, 1997, now U.S. Pat. No. 5,874,266, each of which is incorporated by reference herein.

This invention was made with government support under grant number 4R44RR15374-02 awarded by the National Institute of Health of the United States. The United States Government may have certain rights in this invention.

BACKGROUND OF THE INVENTION

This invention relates to methods for cell manipulation and more specifically to methods for transiently permeabilizing a cell so that a variety of exogenous materials, such as expressible foreign DNA, can be loaded into the cell.

Previous loading methods have included chemical treatments, microinjection, electroporation and particle bombardment. However, these techniques can be time-consuming and suffer from low yields or poor cell survival. Another technique termed "optoporation" has used light directed toward cells and the surrounding media to induce shock waves, thereby causing small holes to form temporarily in the surface of nearby cells, allowing materials to non-specifically enter cells in the area. Another technique termed "optoinjection" also uses light, but directs the light to specific cells. Nevertheless, previous light-based implementations techniques have suffered from the same disadvantages as other loading techniques.

Thus, there is a need for a method for rapid and efficient loading of a variety of exogenous molecules into cells, with high cell survival rates. The present invention satisfies this need and provides related advantages as well.

SUMMARY OF THE INVENTION

The present invention provides optoinjection methods for transiently permeabilizing a target cell. In the general method, the steps are (a) illuminating a population of cells contained in a frame; (b) detecting at least one property of light directed from the frame; (c) locating a target cell by the property of light; and (d) irradiating the target cell with a pulse of radiation.

In particular embodiments, a static representation is obtained when the population of cells is substantially stationary; the cells are illuminated through a lens having a numerical aperture of at most 0.5; the pulse of radiation has a diameter of at least 10 microns at the point of contact with the target cell; or the resulting pulse of radiation delivers at most 1 $\mu J/\mu m^2$. As a result, the method provides rapid and efficient loading of a variety of exogenous molecules into cells, with high cell survival rates.

BRIEF DESCRIPTION OF THE DRAWINGS

FIG. 9 illustrates that the efficiency of optoinjection is energy dose-dependent FIG. 10 compares expression of a plasmid in optoinjected cells (10B) compared to control cells without optoinjection (10A).

DETAILED DESCRIPTION

Figure 1:
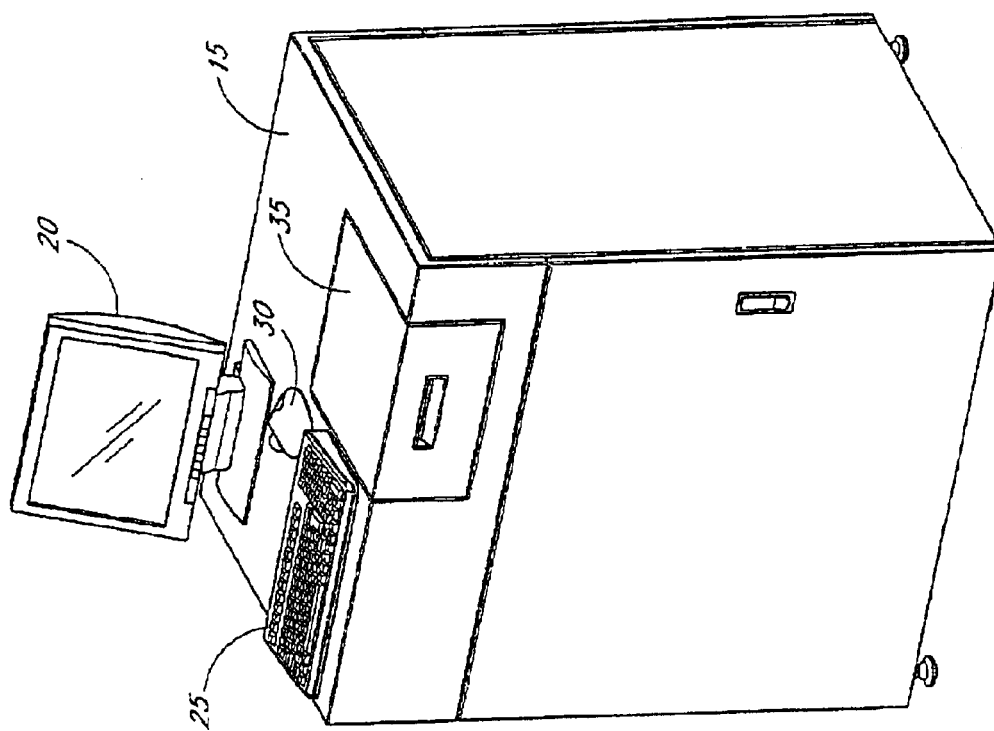
FIG. 1 is a perspective view of one embodiment of a cell treatment apparatus and illustrates the outer design of the housing and display.

A method and apparatus is described for selectively identifying, and individually targeting with an energy beam, specific cells within a cell population for the purpose of inducing a response in the targeted cells. The population of cells can be a mixed population or homogenous in origin. The responses of any of the embodiments of the methods and apparatuses of the invention can be lethal or non-lethal. Examples of such responses are set forth above and throughout this disclosure. The cells targeted can be labeled as is often the case when the specimen is a mixed population. On the other hand, when the specimen is homogenous, the targeted cells can be those individual cells that are being interrogated or intersected by the illumination source or the energy beam, in order to study the response of the cell. For instance, such responses include the morphological or physiological characteristics of the cell. Generally, the method first employs a label that acts as a marker to identify and locate individual cells of a first population of cells within a cell mixture that is comprised of the first population of cells and a second population of cells. The cells targeted by the apparatus and methods herein are those that are selectively labeled, in the case of a mixed population of cells, or the ones undergoing interrogation or intersection by the illumination source or energy beam.

The chosen label can be any that substantially identifies and distinguishes the first population of cells from the second population of cells. For example, monoclonal antibodies that are directly or indirectly tagged with a fluorochrome can be used as specific labels. Other examples of cell surface binding labels include non-antibody proteins, lectins, carbohydrates, or short peptides with selective cell binding capacity. Membrane intercalating dyes, such as PKH-2 and PKH-26, could also serve as a useful distinguishing label indicating mitotic history of a cell. Many membrane-permeable reagents are also available to distinguish living cells from one another based upon selected criteria. For example, phalloidin indicates membrane integrity, tetramethyl rhodamine methyl ester (TMRM) indicates mitochondrial transmembrane potential, monochlorobimane indicates glutathione reductive stage, carboxymethyl fluorescein diacetate (CMFDA) indicates thiol activity, carboxyfluorescein diacetate indicates intracellular pH, fura-2 indicates intracellular $Ca^{2+}$ level, and 5,5',6,6'- tetrachloro-1,1',3,3'-tetraethylbenzimidazolo carbocyanine iodide (JC-1) indicates membrane potential. Cell viability can be assessed by the use of fluorescent SYTO 13 or YO PRO reagents. Similarly, a fluorescently-tagged genetic probe (DNA or RNA) could be used to label cells which carry a gene of interest, or express a gene of interest. Further, cell cycle status could be assessed through the use of Hoechst 33342 dye to label existing DNA combined with bromodeoxyuridine (BrdU) to label newly synthesized DNA.

It should be noted that if no specific label is available for cells of the first population, the method can be implemented in an inverse fashion by utilizing a specific label for cells of the second population. For example, in hematopoietic cell populations, the CD34 or ACC-133 cell markers can be used to label only the primitive hematopoietic cells, but not the other cells within the mixture. In this embodiment, cells of the first population are identified by the absence of the label, and are thereby targeted by the energy beam.

After cells of the first population are identified, an energy beam, such as from a laser, collimated or focused non-laser light, RF energy, accelerated particle, focused ultrasonic energy, electron beam, or other radiation beam, is used to deliver a targeted dose of energy that induces the pre-determined response in each of the cells of the first population, without substantially affecting cells of the second population.

One such pre-determined response is photobleaching. In photobleaching, a label in the form of a dye, such as rhodamine 123, GFP, fluorescein isothiocyanate (FITC), or phycoerythrin, is added to the specimen before the instant methods are commenced. After the population of cells has time to interact with the dye, the energy beam is used to bleach a region of individual cells in the population. Such photobleaching studies can be used to study the motility, replenishment, dynamics and the like of cellular components and processes.

Another response is internal molecular uncaging. In such a process, the specimen is combined with a caged molecule prior to the commencement of the instant methods. Such caged molecules include the β-2,6-dinitrobenzyl ester of L-aspartic acid or the 1-(2-nitrophenyl)ethyl ether of 8-hydroxypyrene-1,3,6-tris-sulfonic acid. Similarly, caging groups including alphacarboxyl-2-nitrobenzyl (CNB) and 5-carboxylmethoxy-2-nitrobenzyl (CMNB) can be linked to biologically active molecules as ethers, thioethers, esters, amines, or similar functional groups. The term "internal molecular uncaging" refers to the fact that the molecular uncaging takes place on the surface or within the cell. Such uncaging experiments study rapid molecular processes such as cell membrane permeability and cellular signaling.

Yet another response is external molecular uncaging. This uses approximately the same process as internal molecular caging. However, in external molecular uncaging, the uncaged molecule is not attached to or incorporated into the targeted cells. Instead, the responses of the surrounding targeted cells to the caged and uncaged variants of the molecule are imaged by the instant apparatus and methods.

FIG. 1 is an illustration of one embodiment of a cell treatment apparatus 10. The cell treatment apparatus 10 includes a housing 15 that stores the inner components of the apparatus. The housing includes laser safety interlocks to ensure safety of the user, and also limits interference by external influences (e.g., ambient light, dust, etc.). Located on the upper portion of the housing 15 is a display unit 20 for displaying captured images of cell populations during treatment. These images are captured by a camera, as will be discussed more specifically below. A keyboard 25 and mouse 30 are used to input data and control the apparatus 10. An access door 35 provides access to a movable stage that holds a specimen container of cells undergoing treatment.

Figure 2:
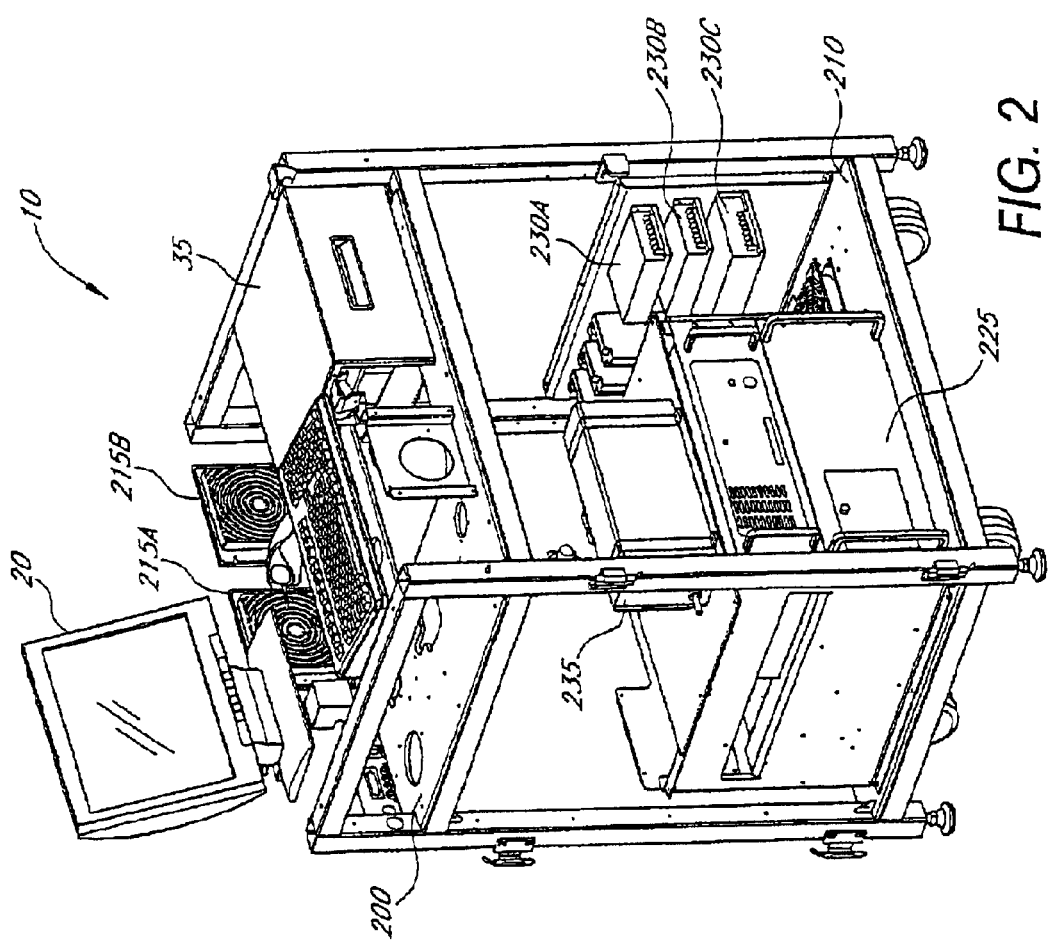
FIG. 2 is a perspective view of one embodiment of a cell treatment apparatus with the outer housing removed and the inner components illustrated.

An interior view of the apparatus 10 is provided in FIG. 2. As illustrated, the apparatus 10 provides an upper tray 200 and lower tray 210 that hold the interior components of the apparatus. The upper tray 200 includes a pair of intake filters 215A,B that filter ambient air being drawn into the interior of the apparatus 10. Below the access door 35 is the optical subassembly (not shown). The optical subassembly is mounted to the upper tray 200 and is discussed in detail with regard to FIGS. 3 to 6.

On the lower tray 210 is a computer 225 which stores the software programs, commands and instructions that run the apparatus 10. In addition, the computer 225 provides control signals to the treatment apparatus through electrical signal connections for steering the laser to the appropriate spot on the specimen in order to treat the cells.

As illustrated, a series of power supplies 230A,B,C provide power to the various electrical components within the apparatus 10. In addition, an uninterruptable power supply 235 is incorporated to allow the apparatus to continue functioning through short external power interruptions.

Figure 3:
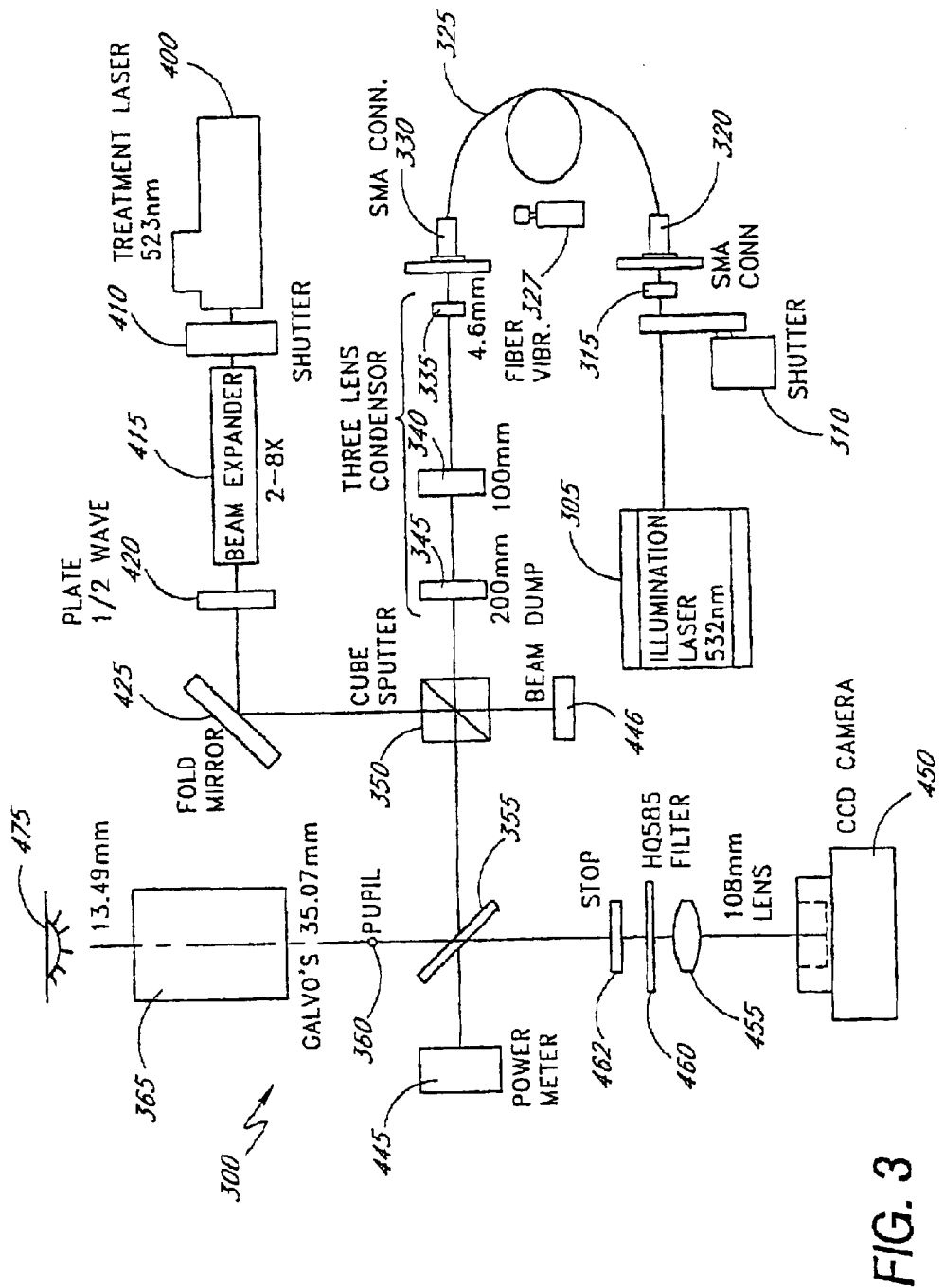
FIG. 3 is a block diagram of the optical subassembly design within one embodiment of a cell treatment apparatus.

FIG. 3 provides a layout of one embodiment of an optical subassembly design 300 within an embodiment of a cell treatment apparatus 10. As illustrated, an illumination laser 305 provides a directed laser output that is used to excite a particular label that is attached to targeted cells within the specimen. In this embodiment, the illumination laser emits light at a wavelength of 532 nm. Once the illumination laser has generated a light beam, the light passes into a shutter 310 which controls the pulse length of the laser light.

After the illumination laser light passes through the shutter 310, it enters a ball lens 315 where it is focused into a SMA fiber optic connector 320. After the illumination laser beam has entered the fiber optic connector 320, it is transmitted through a fiber optic cable 325 to an outlet 330. By passing the illumination beam through the fiber optic cable 325, the illumination laser 305 can be positioned anywhere within the treatment apparatus and thus is not limited to only being positioned within a direct light pathway to the optical components. In one embodiment, the fiber optic cable 325 is connected to a vibrating motor 327 for the purpose of mode scrambling and generating a more uniform illumination spot.

After the light passes through the outlet 330, it is directed into a series of condensing lenses in order to focus the beam to the proper diameter for illuminating one frame of cells. As used herein, one frame of cells is defined as the portion of the biological specimen that is captured within one frame image captured by the camera. This is described more specifically below.

Accordingly, the illumination laser beam passes through a first condenser lens 335. In one embodiment, this first lens has a focal length of 4.6 mm. The light beam then passes through a second condenser lens 340 which, in one embodiment, provides a 100 mm focal length. Finally, the light beam passes into a third condenser lens 345, which preferably provides a 200 mm focal length. While the present invention has been described using specific condenser lenses, it should be apparent that other similar lens configurations that focus the illumination laser beam to an advantageous diameter would function similarly. Thus, this invention is not limited to the specific implementation of any particular condenser lens system.

Once the illumination laser beam passes through the third condenser lens 345, it enters a cube beam splitter 350 that is designed to transmit the 532 nm wavelength of light emanating from the illumination laser. Preferably, the cube beam splitter 350 is a 25.4 mm square cube (Melles-Griot, Irvine, Calif.). However, other sizes are anticipated to function similarly. In addition, a number of plate beam splitters or pellicle beam splitters could be used in place of the cube beam splitter 350 with no appreciable change in function.

Once the illumination laser light has been transmitted through the cube beam splitter 350, it reaches a long wave pass mirror 355 that reflects the 532 nm illumination laser light to a set of galvanometer mirrors 360 that steer the illumination laser light under computer control to a scanning lens (Special Optics, Wharton, N.J.) 365, which directs the illumination laser light to the specimen (not shown). The galvanometer mirrors are controlled so that the illumination laser light is directed at the proper cell population (i.e. frame of cells) for imaging. The "scanning lens" described in this embodiment of the invention includes a refractive lens. It should be noted that the term "scanning lens" as used in the present invention includes, but is not limited to, a system of one or more refractive or reflective optical elements used alone or in combination. Further, the "scanning lens" may include a system of one or more diffractive elements used in combination with one or more refractive and/or reflective optical elements. One skilled in the art will know how to design a "scanning lens" system in order to illuminate the proper cell population.

The light from the illumination laser is of a wavelength that is useful for illuminating the specimen. In this embodiment, energy from a continuous wave 532 nm Nd:YAG frequency-doubled laser (B&W Tek, Newark, Del.) reflects off the long wave pass mirror (Custom Scientific, Phoenix, Ariz.) and excites fluorescent tags in the specimen. In one embodiment, the fluorescent tag is phycoerythrin. Alternatively, Alexa 532 (Molecular Probes, Eugene, Oreg.) can be used. Phycoerythrin and Alexa 532 have emission spectra with peaks near 580 nm, so that the emitted fluorescent light from the specimen is transmitted via the long wave pass mirror to be directed into the camera. The use of the filter in front of the camera blocks light that is not within the wavelength range of interest, thereby reducing the amount of background light entering the camera.

It is generally known that many other devices could be used in this manner to illuminate the specimen, including, but not limited to, an arc lamp (e.g., mercury, xenon, etc.) with or without filters, a light-emitting diode (LED), other types of lasers, etc. Advantages of this particular laser include high intensity, relatively efficient use of energy, compact size, and minimal heat generation. It is also generally known that other fluorochromes with different excitation and emission spectra could be used in such an apparatus with the appropriate selection of illumination source, filters, and long and/or short wave pass mirrors. For example, allophycocyanin (APC) could be excited with a 633 nm HeNe illumination laser, and fluoroisothiocyanate (FITC) could be excited with a 488 nm Argon illumination laser. One skilled in the art could propose many other optical layouts with various components in order to achieve the objective of this invention.

In addition to the illumination laser 305, an optional treatment laser 400 is present to irradiate the targeted cells once they have been identified by image analysis. Of course, in one embodiment, the treatment induces necrosis of targeted cells within the cell population. As shown, the treatment laser 400 outputs an energy beam of 523 nm that passes through a shutter 410. Although the exemplary laser outputs an energy beam having a 523 nm wavelength, other sources that generate energy at other wavelengths are also within the scope of the present invention.

Once the treatment laser energy beam passes through the shutter 410, it enters a beam expander (Special Optics, Wharton, N.J.) 415 which adjusts the diameter of the energy beam to an appropriate size at the plane of the specimen. Following the beam expander 415 is a half-wave plate 420 which controls the polarization of the beam. The treatment laser energy beam is then reflected off a mirror 425 and enters the cube beam splitter 350. The treatment laser energy beam is reflected by 90 degrees in the cube beam splitter 350, such that it is aligned with the exit pathway of the illumination laser light beam. Thus, the treatment laser energy beam and the illumination laser light beam both exit the cube beam splitter 350 along the same light path. From the cube beam splitter 350, the treatment laser beam reflects off the long wave pass mirror 355, is steered by the galvanometers 360, thereafter contacts the scanning lens 365, and finally is focused upon a targeted cell within the specimen. Again, the "scanning lens" described in this embodiment includes a refractive lens. As previously mentioned, the term "scanning lens" includes, but is not limited to, a system of one or more refractive or reflective optical elements used alone or in combination. Further, the "scanning lens" may include one or more diffractive elements used in combination with one or more refractive and/or reflective elements. One skilled in the art will know how to design a "scanning lens" system in order to focus upon the targeted cell within the specimen.

It should be noted that a small fraction of the illumination laser light beam passes through the long wave pass mirror 355 and enters a power meter sensor (Gentec, Palo Alto, Calif.) 445. The fraction of the beam entering the power sensor 445 is used to calculate the level of power emanating from the illumination laser 305. In an analogous fashion, a small fraction of the treatment laser energy beam passes through the cube beam splitter 350 and enters a second power meter sensor (Gentec, Palo Alto, Calif.) 446. The fraction of the beam entering the power sensor 446 is used to calculate the level of power emanating from the treatment laser 400. The power meter sensors are electrically linked to the computer system so that instructions/commands within the computer system capture the power measurement and determine the amount of energy that was emitted.

The energy beam from the treatment laser is of a wavelength that is useful for achieving a response in the cells. In the example shown, a pulsed 523 nm Nd:YLF frequency-doubled laser is used to heat a localized volume containing the targeted cell, such that it is induced to die within a pre-determined period of time. The mechanism of death is dependent upon the actual temperature achieved in the cell, as reviewed by Niemz, M. H., *Laser-tissue interactions: Fundamentals and Applications* (Springer-Verlag, Berlin 1996).

A Nd:YLF frequency-doubled, solid-state laser (Spectra-Physics, Mountain View, Calif.) is used because of its stability, high repetition rate of firing, and long time of maintenance-free service. However, most cell culture fluids and cells are relatively transparent to light in this green wavelength, and therefore a very high fluence of energy would be required to achieve cell death. To significantly reduce the amount of energy required, and therefore the cost and size of the treatment laser, a dye is purposefully added to the specimen to efficiently absorb the energy of the treatment laser in the specimen. In the example shown, the non-toxic dye FD&C red #40 (allura red) is used to absorb the 523 nm energy from the treatment laser, but one skilled in the art could identify other laser/dye combinations that would result in efficient absorption of energy by the specimen. For example, a 633 nm HeNe laser's energy would be efficiently absorbed by FD&C green #3 (fast green FCF), a 488 nm Argon laser's energy would be efficiently absorbed by FD&C yellow #5 (sunset yellow FCF), and a 1064 nm Nd:YAG laser's energy would be efficiently absorbed by Filtron (Gentex, Zeeland, Mich.) infrared absorbing dye. Through the use of an energy absorbing dye, the amount of energy required to kill a targeted cell can be reduced since more of the treatment laser energy is absorbed in the presence of such a dye.

Another method of achieving thermal killing of cells without the addition of a dye involves the use of an ultraviolet laser. Energy from a 355 nm Nd:YAG frequency-tripled laser will be absorbed by nucleic acids and proteins within the cell, resulting in thermal heating and death. Yet another method of achieving thermal killing of cells without the addition of a dye involves the use of a near-infrared laser. Energy from a 2100 nm Ho:YAG laser or a 2940 nm Er:YAG laser will be absorbed by water within the cell, resulting in thermal heating and death.

Although this embodiment describes the killing of cells via thermal heating by the energy beam, one skilled in the art would recognize that other responses can also be induced in the cells by an energy beam, including photomechanical disruption, photodissociation, photoablation, and photochemical reactions, as reviewed by Niemz (Niemz, supra). For example, a photosensitive substance (e.g., hematoporphyrin derivative, tin-etiopurpurin, lutetium texaphyrin) (Oleinick and Evans, The photobiology of photodynamic therapy: Cellular targets and mechanisms, *Rad. Res.* 150: S146–S156 (1998)) within the cell mixture could be specifically activated in targeted cells by irradiation. Additionally, a small, transient pore could be made in the cell membrane (Palumbo et al., Targeted gene transfer in eukaryotic cells by dye-assisted laser optoporation, *J. Photochem. Photobiol.* 36:41–46 (1996)) to allow the entry of genetic or other material. Further, specific molecules in or on the cell, such as proteins or genetic material, could be inactivated by the directed energy beam (Grate and Wilson, Laser-mediated, site-specific inactivation of RNA transcripts, *PNAS* 96:6131–6136 (1999); Jay, D. G., Selective destruction of protein function by chromophore-assisted laser inactivation, *PNAS* 85:5454–5458 (1988)). Also, photobleaching can be utilized to measure intracellular movements such as the diffusion of proteins in membranes and the movements of microtubules during mitosis (Ladha et al., *J. Cell Sci.*, 110(9):1041 (1997); Centonze and Borisy, *J. Cell Sci.* 100 (part 1):205 (1991); White and Stelzer, *Trends Cell Biol.* 9(2):61–5 (1999); Meyvis, et al., *Pharm. Res.* 16(8):1153–62 (1999). Further, photolysis or uncaging, including multiphoton uncaging, of caged compounds can be utilized to control the release, with temporal and spacial resolution, of biologically active products or other products of interest (Theriot and Mitchison, *J. Cell Biol.* 119:367 (1992); Denk, *PNAS* 91(14):6629 (1994)). These mechanisms of inducing a response in a targeted cell via the use of electromagnetic radiation directed at specific targeted cells are also intended to be incorporated into the present invention.

In addition to the illumination laser 305 and treatment laser 400, the apparatus includes a camera 450 that captures images (i.e. frames) of the cell populations. As illustrated in FIG. 3, the camera 450 is focused through a lens 455 and filter 460 in order to accurately record an image of the cells without capturing stray background images. A stop 462 is positioned between the filter 460 and mirror 355 in order to eliminate light that may enter the camera from angles not associated with the image from the specimen. The filter 460 is chosen to only allow passage of light within a certain wavelength range. This wavelength range includes light that is emitted from the targeted cells upon excitation by the illumination laser 305, as well as light from a back-light source 475.

The back-light source 475 is located above the specimen to provide back-illumination of the specimen at a wavelength different from that provided by the illumination laser 305. This LED generates light at 590 nm, such that it can be transmitted through the long wave pass mirror to be directed into the camera. This back-illumination is useful for imaging cells when there are no fluorescent targets within the frame being imaged. An example of the utility of this back-light is its use in attaining proper focus of the system, even when there are only unstained, non-fluorescent cells in the frame. In one embodiment, the back-light is mounted on the underside of the access door 35 (FIG. 2).

Thus, as discussed above, the only light returned to the camera is from wavelengths that are of interest in the specimen. Other wavelengths of light do not pass through the filter 460, and thus do not become recorded by the camera 450. This provides a more reliable mechanism for capturing images of only those cells of interest. It is readily apparent to one skilled in the art that the single filter 460 could be replaced by a movable filter wheel that would allow different filters to be moved in and out of the optical pathway. In such an embodiment, images of different wavelengths of light could be captured at different times during cell processing, allowing the use of multiple cell labels.

It should be noted that in this embodiment, the camera is a charge-coupled device (CCD) and transmits images back to the computer system for processing. As will be described below, the computer system determines the coordinates of the targeted cells in the specimen by reference to the image captured by the CCD camera.

Figure 4:
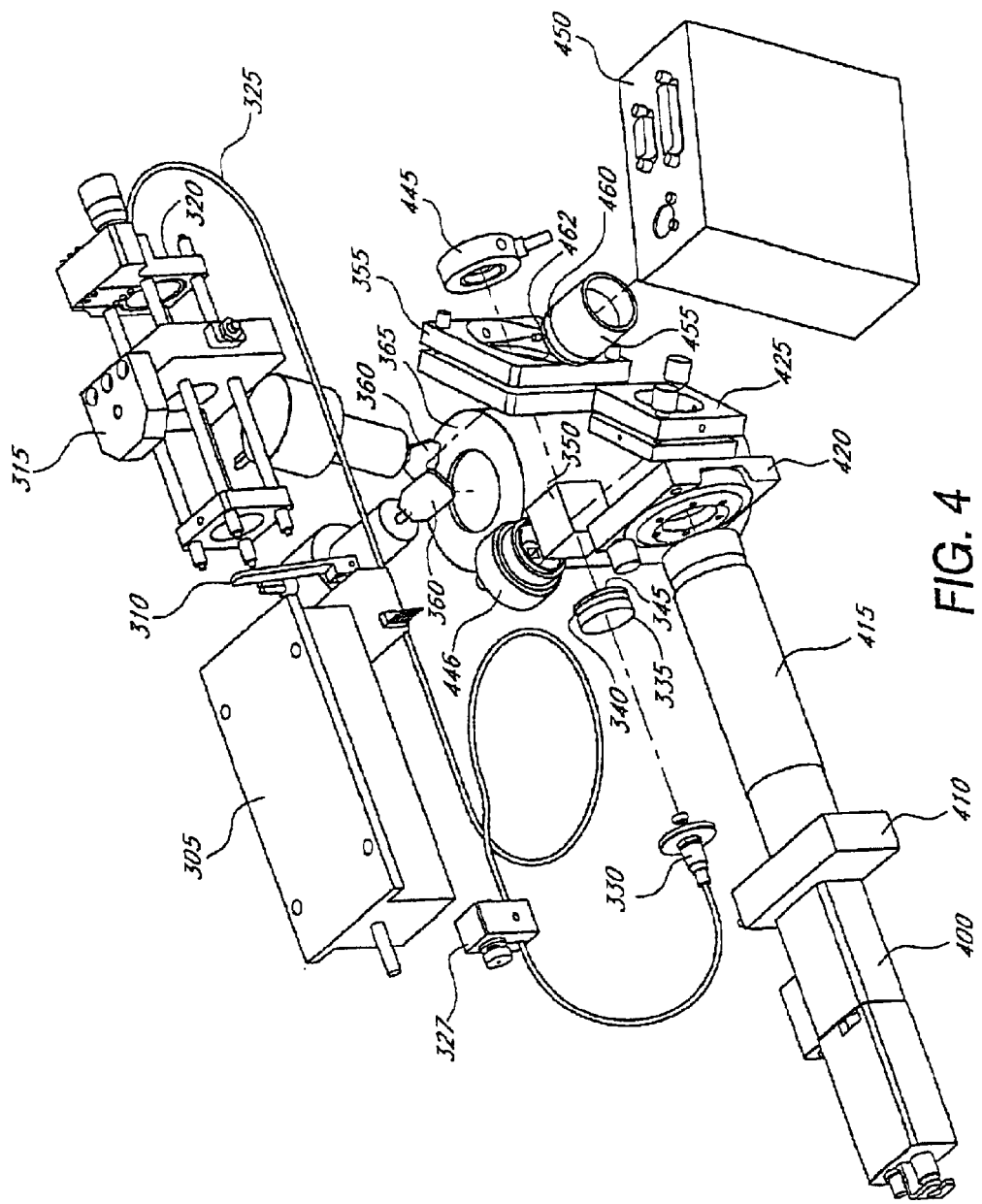
FIG. 4 is a perspective view of one embodiment of an optical subassembly within one embodiment of a cell treatment apparatus.

Referring now to FIG. 4, a perspective view of an embodiment of an optical subassembly is illustrated. As illustrated, the illumination laser 305 sends a light beam through the shutter 310 and ball lens 315 to the SMA fiber optic connector 320. The light passes through the fiber optic cable 325 and through the output 330 into the condenser lenses 335, 340 and 345. The light then enters the cube beam splitter 350 and is transmitted to the long wave pass mirror 355. From the long wave pass mirror 355, the light beam enters the computer-controlled galvanometers 360 and is then steered to the proper frame of cells in the specimen from the scanning lens 365.

As also illustrated in the perspective drawing of FIG. 4, the treatment laser 400 transmits energy through the shutter 410 and into the beam expander 415. Energy from the treatment laser 400 passes through the beam expander 415 and passes through the half-wave plate 420 before hitting the fold mirror 425, entering the cube beam splitter 350 where it is reflected 90 degrees to the long wave pass mirror 355, from which it is reflected into the computer controlled galvanometer mirrors 360. After being steered by the galvanometer mirrors 360 to the scanning lens 365, the laser energy beam strikes the proper location within the cell population in order to induce a response in a particular targeted cell.

Figure 5:
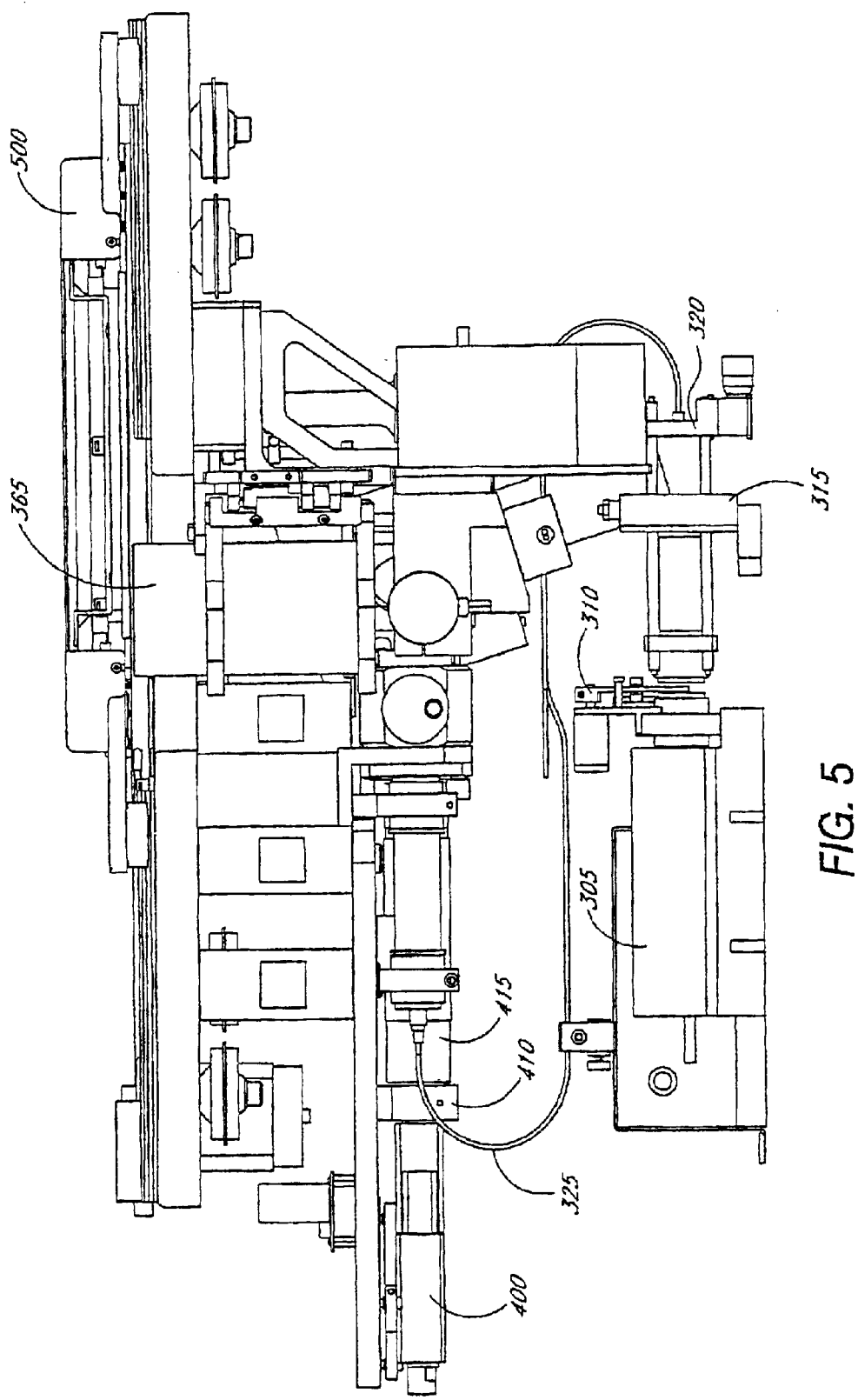
FIG. 5 is a side view of one embodiment of an optical subassembly that illustrates the arrangement of the scanning lens and the movable stage.

In order to accommodate a very large surface area of specimen to treat, the apparatus includes a movable stage that mechanically moves the specimen container with respect to the scanning lens. Thus, once a specific sub-population (i.e. field) of cells within the scanning lens field-of-view has been treated, the movable stage brings another sub-population of cells within the scanning lens field-of-view. As illustrated in FIG. 5, a computer-controlled movable stage 500 holds a specimen container (not shown) to be processed. The movable stage 500 is moved by computer-controlled servo motors along two axes so that the specimen container can be moved relative to the optical components of the instrument. The stage movement along a defined path is coordinated with other operations of the apparatus. In addition, specific coordinates can be saved and recalled to allow return of the movable stage to positions of interest. Encoders on the x and y movement provide closed-loop feedback control on stage position.

The flat-field (F-theta) scanning lens 365 is mounted below the movable stage. The scanning lens field-of-view comprises the portion of the specimen that is presently positioned above the scanning lens by the movable stage 500. The lens 365 is mounted to a stepper motor that allows the lens 365 to be automatically raised and lowered (along the z-axis) for the purpose of focusing the system.

Figure 6:
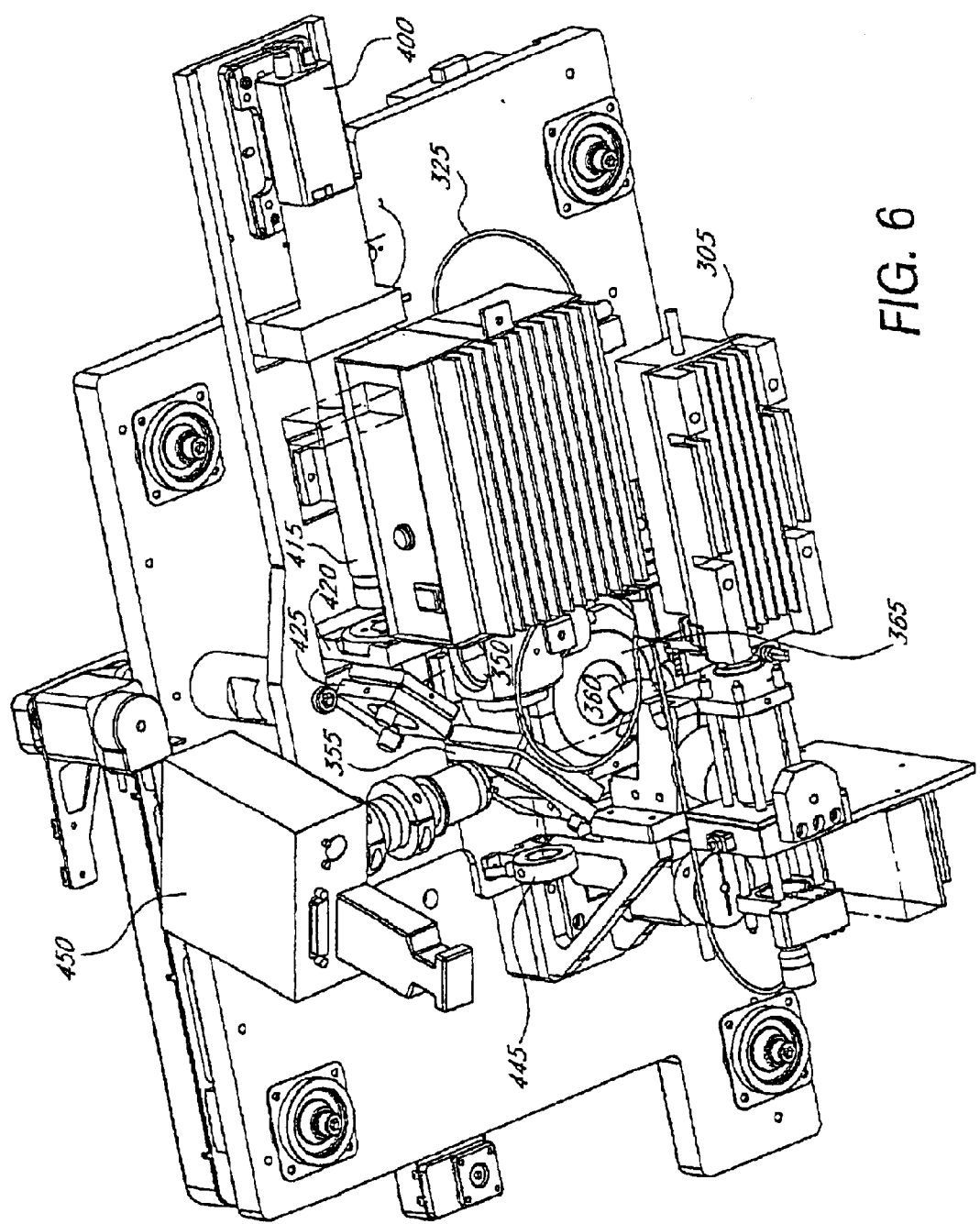
FIG. 6 is a bottom perspective view of one embodiment of an optical subassembly.

As illustrated in FIGS. 4 to 6, below the scanning lens 365 are the galvanometer-controlled steering mirrors 360 that deflect electromagnetic energy along two perpendicular axes. Behind the steering mirrors is the long wave pass mirror 355 that reflects electromagnetic energy of a wavelength shorter than 545 nm. Wavelengths longer than 545 nm are passed through the long wave pass mirror, directed through the filter 460, coupling lens 455, and into the CCD camera, thereby producing an image of the appropriate size on the CCD sensor of the camera 450 (see FIGS. 3 and 4). The magnification defined by the combination of the scanning lens 365 and coupling lens 455 is chosen to reliably detect single cells while maximizing the area viewed in one frame by the camera. Although a CCD camera (DVC, Austin, Tex.) is illustrated in this embodiment, the camera can be any type of detector or image gathering equipment known to those skilled in the art. The optical subassembly of the apparatus is preferably mounted on a vibration-isolated platform to provide stability during operation as illustrated in FIGS. 2 and 5.

Figure 7:
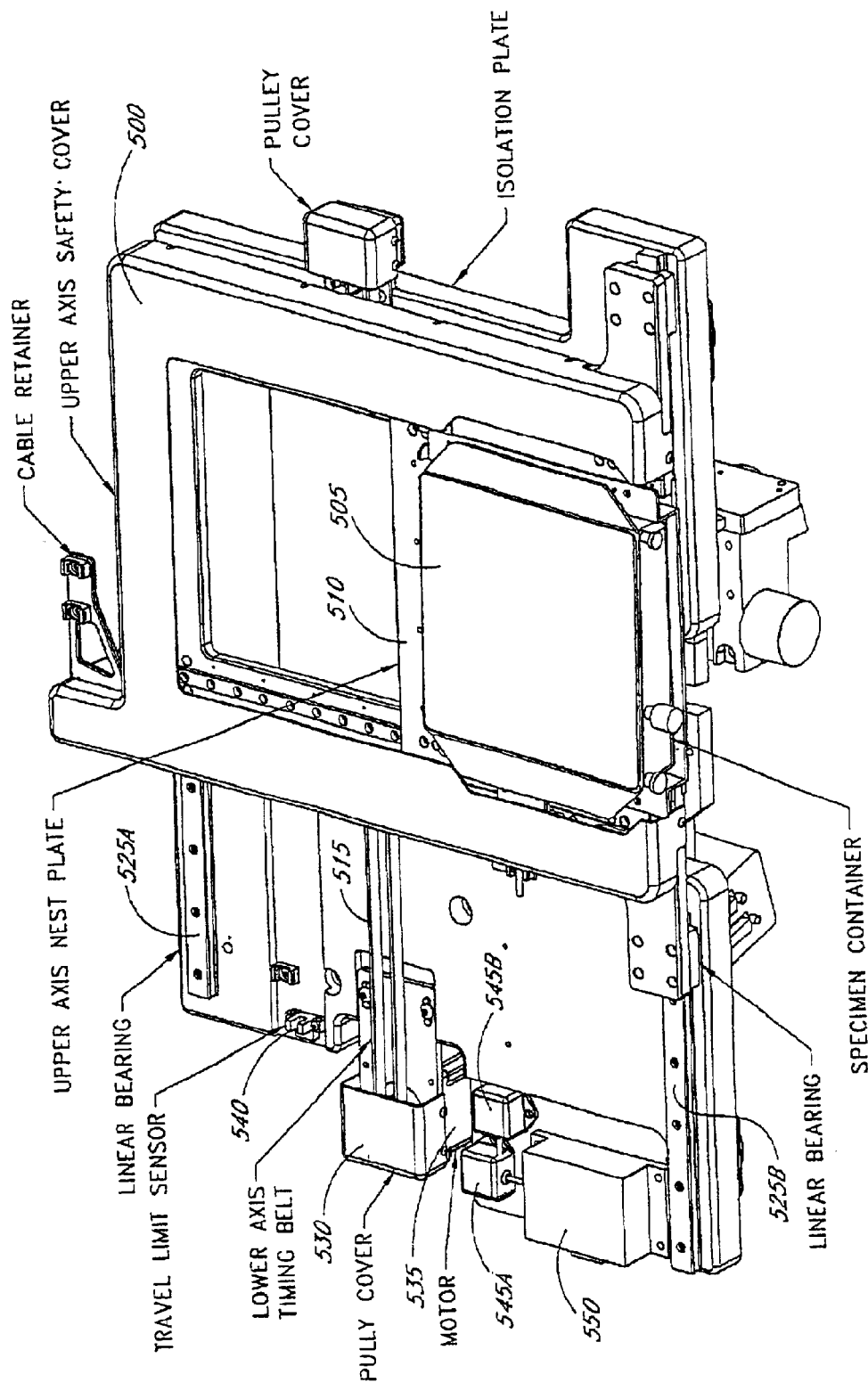
FIG. 7 is a top perspective view of the movable stage of the cell treatment apparatus.

Referring now to FIG. 7, a top view of the movable stage 500 is illustrated. As shown, a specimen container is mounted in the movable stage 500. The specimen container 505 rests on an upper axis nest plate 510 that is designed to move in the forward/backward direction with respect to the movable stage 500. A stepper motor (not shown) is connected to the upper axis nest plate 510 and computer system so that commands from the computer cause forward/backward movement of the specimen container 505.

The movable stage 500 is also connected to a timing belt 515 that provides side-to-side movement of the movable stage 500 along a pair of bearing tracks 525A,B. The timing belt 515 attaches to a pulley (not shown) housed under a pulley cover 530. The pulley is connected to a stepper motor 535 that drives the timing belt 515 to result in side-to-side movement of the movable stage 500. The stepper motor 535 is electrically connected to the computer system so that commands within the computer system result in side-to-side movement of the movable stage 500. A travel limit sensor 540 connects to the computer system and causes an alert if the movable stage travels beyond a predetermined lateral distance.

A pair of accelerometers 545A,B is preferably incorporated on this platform to register any excessive bumps or vibrations that may interfere with the apparatus operation. In addition, a two-axis inclinometer 550 is preferably incorporated on the movable stage to ensure that the specimen container is level, thereby reducing the possibility of gravity-induced motion in the specimen container.

The specimen chamber has a fan with ductwork to eliminate condensation on the specimen container, and a thermocouple to determine whether the specimen chamber is within an acceptable temperature range. Additional fans are provided to expel the heat generated by the electronic components, and appropriate filters are used on the air intakes 215A,B.

The computer system 225 controls the operation and synchronization of the various pieces of electronic hardware described above. The computer system can be any commercially available computer that can interface with the hardware. One example of such a computer system is an Intel Pentium II, III or IV-based computer running the Microsoft WINDOWS NT operating system. Software is used to communicate with the various devices, and control the operation in the manner that is described below.

When the apparatus is first initialized, the computer loads files from the hard drive into RAM for proper initialization of the apparatus. A number of built-in tests are automatically performed to ensure the apparatus is operating properly, and calibration routines are executed to calibrate the apparatus. Upon successful completion of these routines, the user is prompted to enter information via the keyboard and mouse regarding the procedure that is to be performed. Once the required information is entered, the user is prompted to open the access door 35 and load a specimen onto the movable stage.

Once a specimen is in place on the movable stage and the door is closed, the computer passes a signal to the stage to move into a home position. The fan is initialized to begin warming and defogging of the specimen. During this time, cells within the specimen are allowed to settle to the bottom surface. In addition, during this time, the apparatus may run commands that ensure that the specimen is properly loaded, and is within the focal range of the system optics. For example, specific markings on the specimen container can be located and focused on by the system to ensure that the scanning lens has been properly focused on the bottom of the specimen container. Such markings could also be used by the instrument to identify the container, its contents, and even the procedure to be performed. After a suitable time, the computer turns off the fan to prevent excess vibrations during treatment, and cell processing begins.

First, the computer instructs the movable stage to be positioned over the scanning lens so that the first area (i.e. field) of the specimen to be treated is directly in the scanning lens field-of-view. The galvanometer mirrors are instructed to move such that the center frame within the field-of-view is imaged in the camera. As discussed below, the field imaged by the scanning lens is separated into a plurality of frames. Each frame is the proper size so that the cells within the frame are effectively imaged by the camera.

The back-light 475 is then activated in order to illuminate the field-of-view so that it can be brought into focus by the scanning lens. Once the scanning lens has been properly focused upon the specimen, the computer system divides the field-of-view into a plurality of frames so that each frame is analyzed separately by the camera. This methodology allows the apparatus to process a plurality of frames within a large field-of-view without moving the mechanical stage. Because the galvanometers can move from one frame to the next very rapidly compared to the mechanical steps involved in moving the stage, this method results is an extremely fast and efficient apparatus.

Other means of ensuring that the specimen is in focus are also available. For example, a laser proximeter (Cooke Corp., Auburn, Mich.) could rapidly determine the distance between the scanning lens and the sample, and adjust the scanning lens position accordingly. Ultrasonic proximeters are also available, and would achieve the same objective. One skilled in the art could propose other means of ensuring that the specimen is in focus above the scanning lens.

In one preferred embodiment, the apparatus described herein processes at least 1, 2, 3, 4, 5, 6, 7, or 14 square centimeters of a biological specimen per minute. In another embodiment, the apparatus described herein processes at least 0.25, 0.5, 1, 2, 3, 4 or 8 million cells of a biological specimen per minute. In one other embodiment, the apparatus can preferably induce a response in targeted cells at a rate of 50, 100, 150, 200, 250, 300, 350, 400 or 800 cells per second.

Initially, an image of the frame at the center of the field-of-view is captured by the camera and stored to a memory in the computer. Instructions in the computer analyze the focus of the specimen by looking at the size of, number of, and other object features in the image. If necessary, the computer instructs the z-axis motor attached to the scanning lens to raise or lower in order to achieve the best focus. The apparatus may iteratively analyze the image at several z-positions until the best focus is achieved. The galvanometer-controlled mirrors are then instructed to image a first frame, within the field-of-view, in the camera. For example, the entire field-of-view might be divided into 4, 9, 12, 18, 24 or more separate frames that will be individually captured by the camera. Once the galvanometer mirrors are pointed to the first frame in the field-of-view, the shutter in front of the illumination laser is opened to illuminate the first frame through the galvanometer mirrors and scanning lens. The camera captures an image of any fluorescent emission from the specimen in the first frame of cells. Once the image has been acquired, the shutter in front of the illumination laser is closed and a software program (Epic, Buffalo Grove, Ill.) within the computer processes the image.

The power sensor 445 discussed above detects the level of light that was emitted by the illumination laser, thereby allowing the computer to calculate if it was adequate to illuminate the frame of cells. If not, another illumination and image capture sequence is performed. Repeated failure to sufficiently illuminate the specimen will result in an error condition that is communicated to the operator.

Shuttering of illumination light reduces undesirable heating and photobleaching of the specimen and provides a more repeatable fluorescent signal. An image analysis algorithm is run to locate the x-y centroid coordinates of all targeted cells in the frame by reference to features in the captured image. If there are targets in the image, the computer calculates the two-dimensional coordinates of all target locations in relation to the movable stage position and field-of-view, and then positions the galvanometer-controlled mirrors to point to the location of the first target in the first frame of cells. It should be noted that only a single frame of cells within the field-of-view has been captured and analyzed at this point. Thus, there should be a relatively small number of identified targets within this sub-population of the specimen. Moreover, because the camera is pointed to a smaller population of cells, a higher magnification is used so that each target is imaged by many pixels within the CCD camera.

Once the computer system has positioned the galvanometer controlled mirrors to point to the location of the first targeted cell within the first frame of cells, the treatment laser is fired for a brief interval so that the first targeted cell is given an appropriate dose of energy. The power sensor 446 discussed above detects the level of energy that was emitted by the treatment laser, thereby allowing the computer to calculate if it was adequate to induce a response in the targeted cell. If not sufficient, the treatment laser is fired at the same target again. If repeated shots do not deliver the required energy dose, an error condition is communicated to the operator. These targeting, firing, and sensing steps are repeated by the computer for all targets identified in the captured frame.

Once all of the targets have been irradiated with the treatment laser in the first frame of cells, the mirrors are then positioned to the second frame of cells in the field-of-view, and the processing repeats at the point of frame illumination and camera imaging. This processing continues for all frames within the field-of-view above the scanning lens. When all of these frames have been processed, the computer instructs the movable stage to move to the next field-of-view in the specimen, and the process repeats at the back-light illumination and auto-focus step. Frames and fields-of-view are appropriately overlapped to reduce the possibility of inadvertently missing areas of the specimen. Once the specimen has been fully processed, the operator is signaled to remove the specimen, and the apparatus is immediately ready for the next specimen.

Although the text above describes the analysis of fluorescent images for locating targets, one can easily imagine that the non-fluorescent back-light LED illumination images will be useful for locating other types of targets as well, even if they are unlabeled.

The advantage of using the galvanometer mirrors to control the imaging of successive frames and the irradiation of successive targets is significant. One brand of galvanometer is the Cambridge Technology, Inc. model number 6860 (Cambridge, Mass.). This galvanometer can reposition very accurately within a few milliseconds, making the processing of large areas and many targets possible within a reasonable amount of time. In contrast, the movable stage is relatively slow, and is therefore used only to move specified areas of the specimen into the scanning lens field-of-view. Error signals continuously generated by the galvanometer control boards are monitored by the computer to ensure that the mirrors are in position and stable before an image is captured, or before a target is fired upon, in a closed-loop fashion.

In the context of the present invention, the term "specimen" has a broad meaning. It is intended to encompass any type of biological sample placed within the apparatus. The specimen may be enclosed by, or associated with, a container to maintain the sterility and viability of the cells. Further, the specimen may incorporate, or be associated with, a cooling apparatus to keep it above or below ambient temperature during operation of the methods described herein. The specimen container, if one is used, must be compatible with the use of the illumination laser, back-light illuminator, and treatment laser, such that it transmits adequate energy without being substantially damaged itself.

Of course, many variations of the above-described embodiment are possible, including alternative methods for illuminating, imaging, and targeting the cells. For example, movement of the specimen relative to the scanning lens could be achieved by keeping the specimen substantially stationary while the scanning lens is moved. Steering of the illumination beam, images, and energy beam could be achieved through any controllable reflective or diffractive device, including prisms, piezo-electric tilt platforms, or acousto-optic deflectors. Additionally, the apparatus can image/process from either below or above the specimen. Because the apparatus is focused through a movable scanning lens, the illumination and energy beams can be directed to different focal planes along the z-axis. Thus, portions of the specimen that are located at different vertical heights can be specifically imaged and processed by the apparatus in a three-dimensional manner. The sequence of the steps could also be altered without changing the process. For example, one might locate and store the coordinates of all targets in the specimen, and then return to the targets to irradiate them with energy one or more times over a period of time.

To optimally process the specimen, it should be placed on a substantially flat surface so that a large portion of the specimen appears within a narrow range of focus, thereby reducing the need for repeated auto-focus steps. The density of cells on this surface can, in principle, be at any value. However, the cell density should be as high as possible to minimize the total surface area required for the procedure.

A further embodiment of the invention provides optoinjection methods for transiently permeabilizing a target cell. In the general method, the steps are (a) illuminating a population of cells contained in a frame; (b) detecting at least one property of light directed from the frame; (c) locating a target cell by the property of light; and (d) irradiating the target cell with a pulse of radiation.

The "cells" used in the method can be any biological cells, including procaryotic and eucaryotic cells, such as animal cells, plant cells, yeast cells, human cells and non-human primate cells. The cells can be taken from organisms or harvested from cell cultures. The method can also be applied to permeabilize subcellular organelles.

It follows that the term "population" of cells means a group of more than one of such cells. While performing the method, the population of cells can be presented in a specimen container such as 505.

The cells can also be associated with an exogenous label such as a fluorophore. Other labels useful in the invention have been described in detail above.

The population of cells can be "illuminated" by any source that can provide light energy, including a laser and an arc lamp. The light energy can be of any wavelength, such as visible, ultraviolet and infrared light. When the light is from a laser, such as 400, useful wavelengths can range from 100 nm to 1000 nm, 200 nm to 800 nm, 320 nm to 695 nm, and 330 nm to 605 nm. Particular wavelengths include 349 nm, 355 nm, 488 nm, 523 nm, 532 nm, 580 nm, 590 nm, 633 nm, 1064 nm, 2100 nm and 2940 nm. Other illumination sources include any source for an energy beam, as described in detail above. The light can then be directed by any conventional means, such as mirrors, lenses and beam-splitters, to the population of cells.

Once the cells are illuminated, they can be observed in a "frame." As previously defined, one "frame" of cells is the portion of the biological specimen that is captured within one frame image captured by the camera. A particularly useful frame can have an area of at least 50, 70, 85, 95 or 115 mm$^2$. A useful magnification range for the camera is between 2× and 40× and more particularly between 2.5× and 25× and still more particularly between 5× and 10×.

When the frame is illuminated, one or more properties of light can then be detected from the frame. The detectable properties include light having visible, ultraviolet and infrared wavelengths, the intensity of transmittance and reflectance, fluorescence, linear and circular polarization, and phase-contrast illumination. These properties can be detected by conventional optical devices such as the devices already described in detail above.

The target cell can then be located based on its size, shape and other preselected visual properties, and then irradiated with a pulse of radiation. The radiation then causes a temporary permeabilization of the surface of the target cell. While not limiting the method to a particular mechanism, it is believed that the light causes localized melting or other disruption of the cell membrane's continuity, allowing small pores to form without killing the cell.

As a result of transiently permeabilizing the cells, exogenous molecules in the presence of the cell can then enter the cell, whether by diffusion or other mechanism. The term "presence of the cell" herein as applied to an exogenous molecule means in the area near the cell, such as the surrounding medium, so that if the cell were permeabilized, the exogenous molecule could then enter the cell.

The term "exogenous molecule" herein means any molecule or material that does not naturally occur in the cells of the population. It also includes molecules or materials that may occur naturally in the cell, but in significantly higher concentrations than occur naturally in the cell. Exogenous molecules include nucleic acids, polypeptides, carbohydrates, lipids and small molecules. Particular nucleic acids include RNAs, expression plasmids, expression cassettes and other expressible DNA. Particular polypeptides include antibodies and other proteins, which can be introduced into cells to explore interactions between exogenous and endogenous proteins for applications in proteomics. Other polypeptides include peptides for introduction into antigen-displaying dendritic cells. Particular carbohydrates include non-naturally occurring metabolites, such as isotopically labeled sugars, and polysaccharides, such as labeled dextrans. Particular lipids include preselected lipids for incorporation into the cell membrane or other organelles, as well as liposomes and liposomes containing other exogenous molecules of interest. Particular small molecules include ligands for endogenous receptors to study ligand-receptor binding. Similarly, drugs can be introduced into cells, which, in turn, can be introduced as a delivery device into a patient for therapeutic purposes. The term also encompasses dyes capable of absorbing visible, ultraviolet or infrared light.

Exogenous molecules can have a size of greater than 0.1, 0.2, 0.3, 0.5, 1, 2, 3, 5, 10, 20, 30, 50, 70, 100 or even 200 kiloDaltons. Although the efficiency rate of cells that are loaded with at least one exogenous molecule will vary depending on the size and nature of the exogenous molecule, loading efficiencies can be as high as 5%, 10%, 20%, 50%, 75% or even 90% of the population of cells. It should also be emphasized that the method encompasses techniques where two or more exogenous molecules are loaded into cells simultaneously or sequentially.

Significantly, as result of using the method, greater than 50%, 60%, 70%, 80%, 90%, 95% or even 98% of the irradiated target cells can be viable after completion of the method. Methods for measuring cell survival rates are well known in the art and membrane-permeable reagents for distinguishing living cells have been described above. For example, preselected reagents can be added to the media before, during or after performing the method. Specific examples of useful reagents include Calcein AM as an indicator of viability and Sytox Blue as an indicator for dead cells. Other well-known methods include trypan blue exclusion, propidium iodide and $^{51}$Cr-release assay.

It should be noted that the general method presented above has several alternate embodiments that are particularly useful.

First, the general method can be used when the population of cells is substantially stationary. The term "substantially stationary" herein means that the cells are relatively immobile with respect to the medium and are not in flowing medium, and the cells are not subjected to gross movement of a container; but, they can be subject to vibrations and slight movements that normally occur in a typical laboratory. While the term encompasses cells that are immobilized to a surface or within the medium, substantially stationary cells need not be immobilized or otherwise bound to a surface to be considered substantially stationary. Thus, the term includes cells that have settled to the bottom of a specimen container.

When a population of cells is substantially stationary, it becomes useful to obtain a static representation of the cells in the frame. The term "static representation" herein means a substantially complete image of the cells taken during a fixed and discrete time period, rather than as a continuous image, as in a "live" monitor.

Because the cells are substantially stationary, the static representation can then be used as a reliable indicator of the location of one or more cells at subsequent points in time. Moreover, a static representation can be obtained under one set of conditions and another static representation obtained under a different set of conditions so that the two representations can be compared usefully without undue concern for movement of the cells. For example, an image of the cells under visible light can be compared with a corresponding fluorescence image to identify fluorescently tagged cells of interest among a general population of cells. The static representation can also be used as the basis for computer-aided identification and determination of the location of a target cell of interest, based on any of the light properties discussed above.

Second, the general method can be performed where the population of cells is illuminated through a lens having numerical aperture of at most 0.5, 0.4 or 0.3. The term "numerical aperture" or "N.A." used herein is defined N.A.= n(sin $\mu$), where n is the refractive index of the imaging medium between the lens and the cells, and $\mu$ is one-half of the angular aperture.

As a consequence of using a lens having such a low numerical aperture, the lens can have a greater working distance, such as at least 5, 7 or 10 mm. The term "working distance" herein means the distance between the front of the lens to the object, meaning the nearest surface of the population of cells. A particularly useful lens is a flat-field (F-theta) lens, as exemplified by lens 365, described above. It should be noted that confocal microscopy is not possible under such lens parameters.

Third, the pulse of radiation can have a diameter of at least 2, 5, 7, 10, 15, 20, 25 or 30 microns at the point of contact with the target cell. In most cases, the breadth of the radiation will be much wider than any individual cell. Consequently, the beam of radiation need not be separately targeted to a particular point on a cell or cell surface to be effective, but can be directed to the general area of a cell population without losing effectiveness. As a result, sensitivity to beam steering accuracy is reduced and throughput is dramatically increased.

Fourth, the energy delivered by the pulse of radiation can be limited to at most 2, 1.5, 1, 0.7, 0.5, 0.3, 0.2, 0.1, 0.05, 0.02, 0.01 or even 0.005 $\mu J/\mu m^2$. This has the advantage of increasing the survival rate while maintaining efficient loading rates. Moreover, unlike previous methods, the effective energy levels are low enough to allow the use of common plastic specimen containers without damaging the container.

The general method can also be modified to increase throughput. At the most basic level, the direction of the pulse of radiation can be adjusted to irradiate a second target cell in the population in a given frame. Similarly, subsequent fields of view of the population of cells can be processed as described above. This is especially useful when the population of cells remains in a substantially stationary location relative to the lens. Alternatively, the cells can be moved relative to the lens between applications of the method for further steps of detecting, locating and irradiating cells.

To maximize throughput of the cells, one or more of the steps of the method can be automated, as exemplified by the apparatus described in detail above. For example, each of the steps can be controlled by a microprocessor. Similarly, a static representation can be processed as an image or a data set stored in computer memory. By automating each of the steps, the optoinjection method can irradiate at least 5,000, 10,000, 20,000, 50,000, 70,000, 100,000 or even 150,000 cells per minute.

The following examples illustrate the use of the described method and apparatus in different applications.

EXAMPLE 1

Autologous HSC Transplantation

A patient with a B cell-derived metastatic tumor in need of an autologous HSC transplant is identified by a physician. As a first step in the treatment, the patient undergoes a standard HSC harvest procedure, resulting in collection of approximately $1 \times 10^{10}$ hematopoietic cells with an unknown number of contaminating tumor cells. The harvested cells are enriched for HSC by a commercial immunoaffinity column (ISOLEX 300, Nexell Therapeutics, Irvine, Calif.) that selects for cells bearing the CD34 surface antigen, resulting in a population of approximately $3 \times 10^8$ hematopoietic cells, with an unknown number of tumor cells. The mixed population is thereafter contacted with anti-B cell antibodies (directed against CD20 and CD22) that are conjugated to phycoerythrin. The labeled antibodies specifically bind to the B cell-derived tumor cells.

The mixed cell population is then placed in a sterile specimen container on a substantially flat surface near confluence, at approximately 500,000 cells per square centimeter. The specimen is placed on the movable stage of the apparatus described above, and all detectable tumor cells are identified by reference to phycoerythrin and targeted with a lethal dose of energy from a treatment laser. The design of the apparatus allows the processing of a clinical-scale transplant specimen in under 4 hours. The cells are recovered from the specimen container, washed, and then cryopreserved. Before the cells are reinfused, the patient is given high-dose chemotherapy to destroy the tumor cells in the patient's body. Following this treatment, the processed cells are thawed at 37° C. and are given to the patient intravenously. The patient subsequently recovers with no remission of the original cancer.

EXAMPLE 2

Allogeneic HSC Transplantation

In another embodiment, the significant risk and severity of graft-versus-host disease in the allogeneic HSC transplant setting can be combated. A patient is selected for an allogeneic transplant once a suitable donor is found. Cells are harvested from the selected donor as described in the above example. In this case, the cell mixture is contacted with phycoerythrin-labeled anti-CD3 T-cell antibodies. Alternatively, specific allo-reactive T-cell subsets could be labeled using an activated T-cell marker (e.g. CD69) in the presence of allo-antigen. The cell population is processed by the apparatus described herein, thereby precisely defining and controlling the number of T-cells given to the patient. This type of control is advantageous, because administration of too many T-cells increases the risk of graft-versus-host disease, whereas too few T-cells increases the risk of graft failure and the risk of losing of the known beneficial graft-versus-leukemia effect. The present invention and methods are capable of precisely controlling the number of T-cells in an allogeneic transplant.

EXAMPLE 3

Tissue Engineering

In another application, the present apparatus is used to remove contaminating cells in inocula for tissue engineering applications. Cell contamination problems exist in the establishment of primary cell cultures required for implementation of tissue engineering applications, as described by Langer and Vacanti, Tissue engineering: The challenges ahead, *Sci. Am.* 280:86–89 (1999). In particular, chondrocyte therapies for cartilage defects are hampered by impurities in the cell populations derived from cartilage biopsies. Accordingly, the present invention is used to specifically remove these types of cells from the inocula.

For example, a cartilage biopsy is taken from a patient in need of cartilage replacement. The specimen is then grown under conventional conditions (Brittberg et al., Treatment of deep cartilage defects in the knee with autologous chondrocyte transplantation, *N.E. J. Med.* 331:889–895 (1994)). The culture is then stained with a specific label for any contaminating cells, such as fast-growing fibroblasts. The cell mixture is then placed within the apparatus described and the labeled, contaminating cells are targeted by the treatment laser, thereby allowing the slower growing chondrocytes to fully develop in culture.

EXAMPLE 4

Stem Cell Therapy

Yet another embodiment involves the use of embryonic stem cells to treat a wide variety of diseases. Since embryonic stem cells are undifferentiated, they can be used to generate many types of tissue that would find use in transplantation, such as cardiomyocytes and neurons. However, undifferentiated embryonic stem cells that are implanted can also lead to a jumble of cell types which form a type of tumor known as a teratoma (Pedersen, R. A., Embryonic stem cells for medicine, *Sci. Amer.* 280:68–73 (1999)). Therefore, therapeutic use of tissues derived from embryonic stem cells must include rigorous purification of cells to ensure that only sufficiently differentiated cells are implanted. The apparatus described herein is used to eliminate undifferentiated stem cells prior to implantation of embryonic stem cell-derived tissue in the patient.

EXAMPLE 5

Generation of Human Tumor Cell Cultures

In another embodiment, a tumor biopsy is removed from a cancer patient for the purpose of initiating a culture of human tumor cells. However, the in vitro establishment of primary human tumor cell cultures from many tumor types is complicated by the presence of contaminating primary cell populations that have superior in vitro growth characteristics over tumor cells. For example, contaminating fibroblasts represent a major challenge in establishing many cancer cell cultures. The disclosed apparatus is used to particularly label and destroy the contaminating cells, while leaving the biopsied tumor cells intact. Accordingly, the more aggressive primary cells will not overtake and destroy the cancer cell line.

EXAMPLE 6

Generation of a Specific mRNA Expression Library

The specific expression pattern of genes within different cell populations is of great interest to many researchers, and many studies have been performed to isolate and create libraries of expressed genes for different cell types. For example, knowing which genes are expressed in tumor cells versus normal cells is of great potential value (Cossman, et al., Reed-Sternberg cell genome expression supports a B-cell lineage, *Blood* 94:411–416 (1999)). Due to the amplification methods used to generate such libraries (e.g. PCR), even a small number of contaminating cells will result in an inaccurate expression library (Cossman et al., supra; Schutze and Lahr, Identification of expressed genes by laser-mediated manipulation of single cells, *Nature Biotechnol.* 16:737–742 (1998)). One approach to overcome this problem is the use of laser capture microdissection (LCM), in which a single cell is used to provide the starting genetic material for amplification (Schutze and Lahr, supra). Unfortunately, gene expression in single cells is somewhat stochastic, and may be biased by the specific state of that individual cell at the time of analysis (Cossman et al., supra). Therefore, accurate purification of a significant cell number prior to extraction of mRNA would enable the generation of a highly accurate expression library, one that is representative of the cell population being studied, without biases due to single cell expression or expression by contaminating cells. The methods and apparatus described in this invention can be used to purify cell populations so that no contaminating cells are present during an RNA extraction procedure.

EXAMPLE 7

Transfection of a Specific Cell Population

Many research and clinical gene therapy applications are hampered by the inability to transfect an adequate number of a desired cell type without transfecting other cells that are present. The method of the present invention would allow selective targeting of cells to be transfected within a mixture of cells. By generating a photomechanical shock wave at or near a cell membrane with a targeted energy source, a transient pore can be formed, through which genetic (or other) material can enter the cell. This method of gene transfer has been called optoporation (Palumbo et al. supra). The apparatus described above can achieve selective optoporation on only the cells of interest in a rapid, automated, targeted manner.

For example, white blood cells are plated in a specimen container having a solution containing DNA to be transfected. Fluorescently-labeled antibodies having specificity for stem cells are added into the medium and bind to the stem cells. The specimen container is placed within the cell processing apparatus and a treatment laser is targeted to any cells that become fluorescent under the illumination laser light. The treatment laser facilitates transfection of DNA specifically into the targeted cells.

EXAMPLE 8

Selection of Desirable Clones in a Biotechnology Application

In many biotechnology processes where cell lines are used to generate a valuable product, it is desirable to derive clones that are very efficient in producing the product. This selection of clones is often carried out manually, by inspecting a large number of clones that have been isolated in some manner. The present invention would allow rapid, automated inspection and selection of desirable clones for production of a particular product. For example, hybridoma cells that are producing the greatest amounts of antibody can be identified by a fluorescent label directed against the Fc region. Cells with no or dim fluorescent labeling are targeted by the treatment laser for killing, leaving behind the best producing clones for use in antibody production.

EXAMPLE 9

Automated Monitoring of Cellular Responses

Automated monitoring of cellular responses to specific stimuli is of great interest in high-throughput drug screening. Often, a cell population in one well of a well-plate is exposed to a stimulus, and a fluorescent signal is then captured over time from the cell population as a whole. Using the methods and apparatus described herein, more detailed monitoring could be done at the single cell level. For example, a cell population can be labeled to identify a characteristic of a subpopulation of cells that are of interest. This label is then excited by the illumination laser to identify those cells. Thereafter, the treatment laser is targeted at the individual cells identified by the first label, for the purpose of exciting a second label, thereby providing information about each cell's response. Since the cells are substantially stationary on a surface, each cell could be evaluated multiple times, thereby providing temporal information about the kinetics of each cell's response. Also, through the use of the large area scanning lens and galvanometer mirrors, a relatively large number of wells could be quickly monitored over a short period of time.

As a specific example, consider the case of alloreactive T-cells as presented in Example 2, above. In the presence of allo-antigen, activated donor T-cells could be identified by CD69. Instead of using the treatment laser to target and kill these cells, the treatment laser could be used to examine the intracellular pH of every activated T-cell through the excitation and emitted fluorescence of carboxyfluorescein diacetate. The targeted laser allows the examination of only cells that are activated, whereas most screening methods evaluate the response of an entire cell population. If a series of such wells are being monitored in parallel, various agents could be added to individual wells, and the specific activated T-cell response to each agent could be monitored over time. Such an apparatus would provide a high-throughput screening method for agents that ameliorate the alloreactive T-cell response in graft-versus-host disease. Based on this example, one skilled in the art could imagine many other examples in which a cellular response to a stimulus is monitored on an individual cell basis, focusing only on cells of interest identified by the first label.

EXAMPLE 10

Photobleaching Studies

Photobleaching, and/or photobleach recovery, of a specific area of a fluorescently-stained biological sample is a common method that is used to assess various biological processes. For example, a cell suspension is labeled with rhodamine 123, which fluorescently stains mitochondria within the cells. Using the instant illumination laser, the mitochondria within one or more cells are visualized due to rhodamine 123 fluorescence. The treatment laser is then used to deliver a focused beam of light that results in photobleaching of the rhodamine 123 in a small area within one or more cells. The photobleached area(s) then appear dark immediately thereafter, whereas adjacent areas are unaffected. A series of images are then taken using the illumination laser, providing a time-lapse series of images that document the migration of unbleached mitochondria into the area that was photobleached with the treatment laser This approach can be used to assess the motion, turnover, or replenishment of many biological structures within cells.

Thus, in cultured rat neurites, the photobleach recovery of mitochondria is a measure of the size of the mobile pool of mitochondria within each cell (Chute, et al., Analysis of the steady-state dynamics organelle motion in cultured neurites, *Clin. Exp. Pharmco. Physiol.* 22:360 (1995)). The rate of photobleach recovery in these cells is dependent on intracellular calcium and magnesium concentrations, energy status, and microtubule integrity. Neurotoxic substances, such as taxol or vinblastine, will affect the rate of photobleach recovery. Therefore, an assay for neurotoxic substances could be based on the measurement of photobleach recovery of mitochondria within a statistically significant number of neurites that had been exposed to various agents in the wells of a multi-well plate. In such an application, the apparatus described herein and used as described above, would provide a rapid automated method to assess neurotoxicity of many substances on a large number of cells. Based on this example, one skilled in the art could imagine many other examples in which photobleaching is induced and photobleach recovery is monitored in order to obtain useful information from a biological specimen.

EXAMPLE 11

Uncaging Studies

Use of caged compounds to study rapid biological processes involves the binding (i.e. caging) of a biologically relevant substance in an inactive state, allowing the caged substance to diffuse into the biological specimen (a relatively slow process), and then using a laser to induce a photolysis reaction (a relatively fast process) which liberates (i.e. uncages) the substance in situ over microsecond time scales. The biological specimen is then observed in short time-lapse microscopy in order to determine the effect of the uncaged substance on some biological process. Cages for many important substances have been described, including Dioxygen, cyclic ADP ribose (cADPR), nicotinic acid adenine dinucleotide phosphate (NAADP), nitric oxide (NO), calcium, L-aspartate, and adenosine triphosphate (ATP). Chemotaxis is one example of a physiological characteristic that can be studied by uncaging compounds.

Uncaging studies involve the irradiation of a portion of a biological specimen with laser light followed by examination of the specimen with time-lapse microscopy. The apparatus of the current invention has clear utility in such studies. As a specific example, consider the study of *E. coli* chemotaxis towards L-aspartate (Jasuja et al., Chemotactic responses of *Escherichia coli* to small jumps of photoreleased L-aspartate, *Biophys. J.* 76:1706 (1999)). The beta-2,6-dinitrobenzyl ester of L-aspartic acid and the 1-(2-nitrophenyl)ethyl ether of 8-hydroxylpyrene-1,3,6-trissulfonic acid are added to the wells of a well plate containing *E. coli.* Upon irradiation with the treatment laser, a localized uncaging of L-aspartate and the fluorophore 8-hydroxylpyrene-1,3,6-tris-sulfonic acid (pyranine) is induced. The L-aspartate acts as a chemoattractant for *E. coli.*, and in subsequent fluorescent images (using the illumination laser) the pyranine fluorophore acts as an indicator of the degree of uncaging that has occurred in the local area of irradiation. Time-lapse images of the *E. coli.* in the vicinity illuminated by visible wavelength light, such as from the back-light, of the uncaging event are used to measure the chemotactic response of the microorganisms to the locally uncaged L-aspartate. Due to the nature of the present invention, a large number of wells, each with a potential anti-microbial agent added, are screened in rapid order to determine the chemotactic response of microorganisms. Based on this example, one skilled in the art could imagine many other examples in which uncaging is induced by the treatment laser, followed by time-lapse microscopy in order to obtain useful information on a large number of samples in an automated fashion.

EXAMPLE 12

Optoinjection of NIH-3T3 Cells with 70 kD Dextran

This example illustrates an optoinjection method for transiently permeabilizing a target cell. NIH-3T3 cells were grown in a 96-well plate. The growth medium was removed and replaced with PBS containing 1% BSA and 0.1 mM Texas-Red-Dextran (70 kDa) (Molecular Probes, Eugene, Oreg.). Upon illumination of the cells under broad-spectrum light, a static image (FIG. 8A) was obtained to determine which cells to target.

A 30 micron energy beam having a wavelength of 523 nm was directed sequentially to the target cells through a flat-field lens having a magnification of 2.5×, a numerical aperture (N.A.) of 0.25, and a working distance of greater than 10 mm. Over 500 cells were targeted per second.

Figures 8A, 8B, 8C:
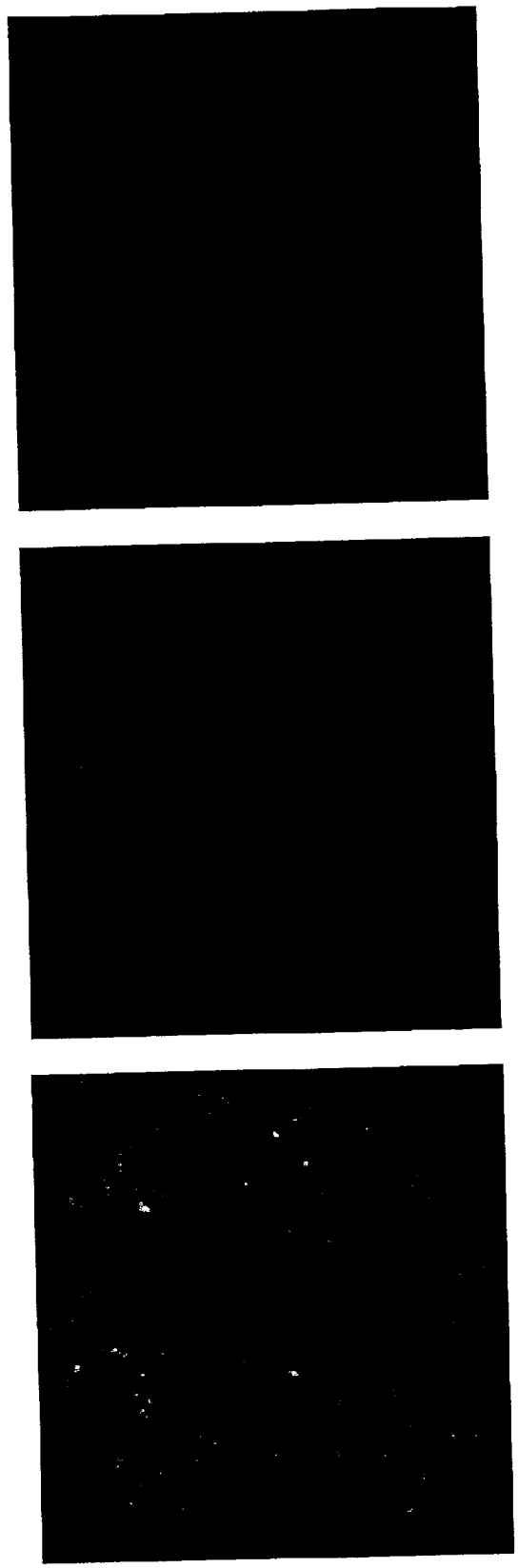
FIG. 8 shows cells under broad-spectrum light (8A), cells showing loading of Texas-Red-Dextran (8B) and nonviable cells (8C).

After irradiating the target cells, the wells were washed, and Sytox Blue (10 mM, Molecular Probes) was added to stain non-viable cells. As shown in FIG. 8B, about 70% of the cells showed loading of the Texas-Red-Dextran as an exogenous molecule. Moreover, only one cell was non-viable (FIG. 8C), equivalent to about a 95% survival rate.

EXAMPLE 13

Optoinjection of SU-DHL-4 Cells with Sytox Green

Using the same hardware apparatus as in Example 12, SU-DHL-4 cells were placed in 96-well plates in PBS with 1% HSA. The membrane-impermeable dye Sytox Green (Molecular Probes) was added at 0.05 mM, the cells were allowed to settle, and then were imaged and targeted with a 30 micron laser beam. Different energy levels ranging from 2 to 15 µJ per pulse of the laser were used in each of five wells, with each target cell receiving one pulse. As show in FIG. 9, the efficiency of optoinjection was energy dose-dependent, ranging from 58% at 4 µJ/cell (0.0057 µJ/µm$^2$) to 92% at 15 µJ/cell (0.021 µJ/µm$^2$). In all cases, cell viability was greater than 95%.

EXAMPLE 14

Optoinjection of 293T Cells with pEGFP-N1 Plasmid

In this experiment, the exogenous molecule was a DNA plasmid of 4.3 kb encoding the fluorescent EGFP protein (pEGFP-N1). The same hardware apparatus was used as in Example 12. The cells were in a medium of PBS and 1% HSA, and then 0.1 microgram of plasmid was added to each well. The cells were imaged, located and targeted with the laser beam such that each cell received 1 to 8 pulses of 15 µJ each (0.021 µJ/µm$^2$). The cells were washed, placed in growth medium, and then cultured for 48 to 96 hours. After culturing, cells were evaluated for the expression of the fluorescent EGFP protein. As shown in FIG. 10, a number of cells displayed the fluorescent phenotype in the treated wells (FIG. 10A), whereas no fluorescence was observed in the control well (FIG. 10B), which were treated identically with the exception of delivering the laser pulses.

Although aspects of the present invention have been described by particular embodiments exemplified herein, the present invention is not so limited. The present invention is only limited by the claims appended below.

We claim:

1. A method for transiently permeabilizing a target cell, comprising the steps of
   (a) illuminating a population of cells contained in a frame;
   (b) detecting at least one property of light directed from the frame;
   (c) locating a target cell in the population of cells, wherein the target cell is located with reference to the detected property of light; and
   (d) irradiating the target cell with a pulse of radiation, wherein the pulse of radiation has a diameter of at least 10 µm at the point of contact with the target cell;
   whereby the target cell is transiently permeabilized.

2. A method for transiently permeabilizing a target cell, comprising the steps of
   (a) illuminating a population of cells contained in a frame;
   (b) detecting at least one property of light directed from the frame;
   (c) locating a target cell in the population of cells, wherein the target cell is located with reference to the detected property of light; and
   (d) irradiating the target cell with a pulse of radiation, wherein the pulse of radiation delivers at most 2 µJ/µm$^2$;
   whereby the target cell is transiently permeabilized.

3. The method of claim 1, wherein the population of cells is substantially stationary.

4. The method of claim 1, wherein the at least one property of light detected in step (b) is obtained as a static representation of light transmitted simultaneously from the frame, whereby the target cell located in step (c) is located with reference to the static representation.

5. The method of claim 1, wherein at least one property of light is fluorescence and the target cell is located with reference to the fluorescence.

6. The method of claim 1, wherein the population of cells is illuminated through a lens having numerical aperture of at most 0.5 and the target cell is located with reference to a property of light directed from the frame and through the lens.

7. The method of claim 2, wherein the pulse of radiation has a diameter of at least 5 µm at the point of contact with the target cell.

8. The method of claim 1, wherein the pulse of radiation has a diameter of at least 20 µm at the point of contact with the target cell.

9. The method of claim 1, wherein the pulse of radiation delivers at most 2 µJ/µm$^2$.

10. The method of claim 2, wherein the pulse of radiation delivers at most 0.1 μJ/μm².

11. The method of claim 2, wherein the pulse of radiation delivers at most 0.01 μJ/μm².

12. The method of claim 2, wherein the pulse of radiation delivers at most 1 μJ/μm².

13. The method of claim 2, wherein the population of cells is substantially stationary.

14. The method of claim 2, wherein the at least one property of light detected in step (b) is obtained as a static representation of light transmitted simultaneously from the frame, whereby the target cell located in step (c) is located with reference to the static representation.

15. The method of claim 2, wherein at least one property of light is fluorescence and the target cell is located with reference to the fluorescence.

16. The method of claim 2, wherein the population of cells is illuminated through a lens having numerical aperture of at most 0.5 and the target cell is located with reference to a property of light directed from the frame and through the lens.

17. The method of claim 2, further comprising the step of (e) adjusting the direction of the pulse of radiation to irradiate a second target cell in the population, whereby the second target cell is transiently permeabilized.

18. The method of claim 2, wherein the frame has an area of at least 50 mm².

19. The method of claim 2, wherein the frame has an area of at least 85 mm².

20. The method of claim 2, wherein the frame has an area of at least 115 mm².

21. The method of claim 2, wherein the property of light is transmittance and the target cell is located with reference to the transmittance.

22. The method of claim 2, wherein the property of light is polarization and the target cell is located with reference to the polarization.

23. The method of claim 2, wherein the property of light is reflectance and the target cell is located with reference to the reflectance.

24. The method of claim 2, wherein the property of light is phase contrast illumination and the target cell is located with reference to the phase contrast illumination.

25. The method of claim 2, wherein the target cell is a procaryotic cell.

26. The method of claim 25, wherein said procaryotic cell is a bacterial cell.

27. The method of claim 2, wherein the target cell is a eucaryotic cell.

28. The method of claim 2, wherein the target cell is selected from the group consisting of an animal cell, plant cell, yeast cell, human cell and non-human primate cell.

29. The method of claim 2, wherein the population of cells contains cells associated with an exogenous label.

30. The method of claim 29, wherein the label is a fluorophore.

31. The method of claim 2, wherein the target cell is associated with an exogenous label.

32. The method of claim 2, wherein the target cell is in the presence of an exogenous molecule.

33. The method of claim 32, wherein the exogenous molecule is selected from the group consisting of a nucleic acid, polypeptide, carbohydrate, lipid, and small molecule.

34. The method of claim 33, wherein the small molecule is a dye capable of absorbing visible, ultraviolet or infrared light.

35. The method of claim 14, wherein step (b) further comprises obtaining a second static representation of at least one property of light directed simultaneously from the frame.

36. The method of claim 35, wherein the target cell is located with reference to the first and second static representations.

37. The method of claim 2, further comprising:
(e) locating additional target cells in the population of cells, wherein the target cells are located with reference to the detected property of light, and
(f) irradiating each of the target cells with a pulse of radiation, wherein the pulse of radiation has a diameter of at least 10 μm at the point of contact with each target cell; whereby additional target cells are transiently permeabilized.

38. The method of claim 37, wherein at least 10,000 cells are irradiated per minute.

39. The method of 37, wherein at least 20,000 cells are irradiated per minute.

40. The method of claim 37, wherein at least 50,000 cells are irradiated per minute.

41. The method of claim 37, wherein at least 100,000 cells are irradiated per minute.

42. The method of claim 2, further comprising the steps of
(e) illuminating a population of cells contained in a second frame,
(f) obtaining a static representation of at least one property of light directed from the second frame, and repeating steps (c) through (d).

43. The method of claim 42, wherein the population of cells remains in a substantially stationary location relative to a lens.

44. The method of claim 42, wherein at least 10,000 cells are irradiated per minute.

45. The method of 42, wherein at least 20,000 cells are irradiated per minute.

46. The method of claim 42, wherein at least 50,000 cells are irradiated per minute.

47. The method of claim 42, wherein at least 100,000 cells are irradiated per minute.

48. The method of claim 42, further comprising the step of
(g) moving the population of cells and repeating steps (a) through (f).

49. The method of claim 42, wherein steps (a) through (f) are automated.

50. The method of claim 2, further comprising the steps of
(e) moving the population of cells relative to a lens and repeating steps (a) through (d).

51. The method of claim 2, wherein steps (a) through (d) are automated.

52. The method of claim 14, wherein the static representation comprises an image.

53. The method of claim 14, wherein the static representation comprises a set of data stored in computer memory.

54. The method of claim 2, further comprising a camera having a magnification between 2× and 40×.

55. The method of claim 2, further comprising a camera having a magnification between 2.5× and 25×.

56. The method of claim 16, wherein the lens has a numerical aperture of at most 0.3.

57. The method of claim 37, wherein the property of light is intensity and the target cell is located with reference to the intensity.

58. The method of claim 37, wherein greater than 50% of the irradiated target cells are viable after the method is performed.

59. The method of claim 37, wherein greater than 80% of the irradiated target cells are viable after the method is performed.

60. The method of claim 37, wherein greater than 90% of the irradiated target cells are viable after the method is performed.

* * * * *